US009052281B2

(12) United States Patent
Jain et al.

(10) Patent No.: US 9,052,281 B2
(45) Date of Patent: Jun. 9, 2015

(54) TRANSISTOR-BASED PARTICLE DETECTION SYSTEMS AND METHODS

(71) Applicant: Purdue Research Foundation, West Lafayette, IN (US)

(72) Inventors: Ankit Jain, West Lafayette, IN (US); Pradeep R. Nair, Mumbai (IN); Muhammad Ashraful Alam, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 13/748,171

(22) Filed: Jan. 23, 2013

(65) Prior Publication Data

US 2013/0187200 A1 Jul. 25, 2013

Related U.S. Application Data

(60) Provisional application No. 61/590,084, filed on Jan. 24, 2012.

(51) Int. Cl.
*G01P 15/08* (2006.01)
*G01N 27/414* (2006.01)

(52) U.S. Cl.
CPC .................................. *G01N 27/4143* (2013.01)

(58) Field of Classification Search
CPC .............. G01L 27/414; G01L 27/4141; G01L 27/4143; G01L 27/4145; G01P 15/08
USPC ..................................... 257/253, 417; 438/49
See application file for complete search history.

(56) References Cited

U.S. PATENT DOCUMENTS

| 6,413,802 | B1 | 7/2002 | Hu et al. | |
|---|---|---|---|---|
| 2009/0321276 | A1* | 12/2009 | Doron et al. | 205/777.5 |
| 2010/0143887 | A1* | 6/2010 | Kim et al. | 435/5 |
| 2010/0244855 | A1* | 9/2010 | Agache et al. | 324/634 |

OTHER PUBLICATIONS

Ankit Jain et al. "Flexure-FET biosensor to break the fundamental sensitivity limits of nanobiosensors using nonlinear electromechanical coupling" School of Electrical and Computer Engineering, approved Mar. 30, 2012, available online May 23, 2012, PNAS, Supporting Information included.
Nicklolay V. Lavrick et al. "Cantilever transducers as a platform for chemical and biological sensors" Review of Scientific Instruments, Review Article, vol. 75 No. 7, Jul. 2004, pp. 2229-2250, © 2004 American Institute of Physics. @DOI: 10.1063/1.1763252#.

(Continued)

*Primary Examiner* — Christine Enad
(74) *Attorney, Agent, or Firm* — Purdue Research Foundation (57) ABSTRACT

Transistor-based particle detection systems and methods may be configured to detect charged and non-charged particles. Such systems may include a supporting structure contacting a gate of a transistor and separating the gate from a dielectric of the transistor, and the transistor may have a near pull-in bias and a sub-threshold region bias to facilitate particle detection. The transistor may be configured to change current flow through the transistor in response to a change in stiffness of the gate caused by securing of a particle to the gate, and the transistor-based particle detection system may configured to detect the non-charged particle at least from the change in current flow.

20 Claims, 11 Drawing Sheets

(56) References Cited

OTHER PUBLICATIONS

J.L. Arlett et al. "Comparative advantages of mechanical biosensors" Nature Nanotechnology, Review Article, vol. 6, Apr. 2011, pp. 203-215, © 2011 Macmillan Publishers Limited. http://www.nature.com/doifinder/10.1038/nnano.2011.44.

P. Bergveld "Thirty years of ISFETOLOGY What happened in the past 30 years and what may happen in the next 30 years" Presented at the 9th IMCS, Boston, 2002. pp. 1-20, MESA Research Institute, University of Twente, P.O. Box 217, 7500 AE Enschede, The Netherlands. © 2002 Elsevier Science B.V.

Pradeep R. Nair et al. "Screening-Limited Response of NanoBiosensors" NANO LETTERS 2008, vol. 8. No. 5 pp. 1281-1285, School of Electrical and Computer Engineering, Purdue University, West Lafayette, Indiana 47907. © 2008 American Chemical Society.

Harvey C. Nathanson et al. "The Resonant Gate Transistor" IEEE Transactions on Electron Devices, vol. Ed-14, No. 3, Mar. 1967. pp. 117-133. Supported in part by the U.S. Air Force Avionics Laboratory, Electronics Technology Division. Westinghouse Research Laboratories, Pittsburgh, PA.

Hei Kam et al. "Pull-In and Release Voltage Design for Nanoelectromechanical Field-Effect Transistors" IEEE Transactions on Electron Devices, vol. 56, No. 12, Dec. 2009. pp. 3072-3082.

* cited by examiner

TRANSISTOR-BASED PARTICLE DETECTION SYSTEMS AND METHODS

CROSS-REFERENCE TO RELATED APPLICATION

This application claims the benefit of U.S. Provisional Application No. 61/590,084, filed Jan. 24, 2012, the entire disclosure of which is hereby incorporated herein by reference.

STATEMENT OF GOVERNMENT INTEREST

This invention was made with government support under Grant No. DE-FC52-08NA28617 awarded by the U.S. Department of Energy. The government has certain rights in the invention.

TECHNICAL FIELD

Some embodiments of this invention pertain to transistor-based particle detection systems and methods. In some embodiments, transistor-based particle detection systems and methods are configured to detect non-charged particles.

BACKGROUND

Some conventional particle detection schemes are label-based and others are label-free. Label-based detection schemes involve labeling the target molecules. Labeling, for example, can be done by attaching a light emitting particle to the target molecule. On the other hand, in label-free detection schemes, some intrinsic property of the target molecule itself is detected, such as the target molecule's mass or charge.

Figure 1:
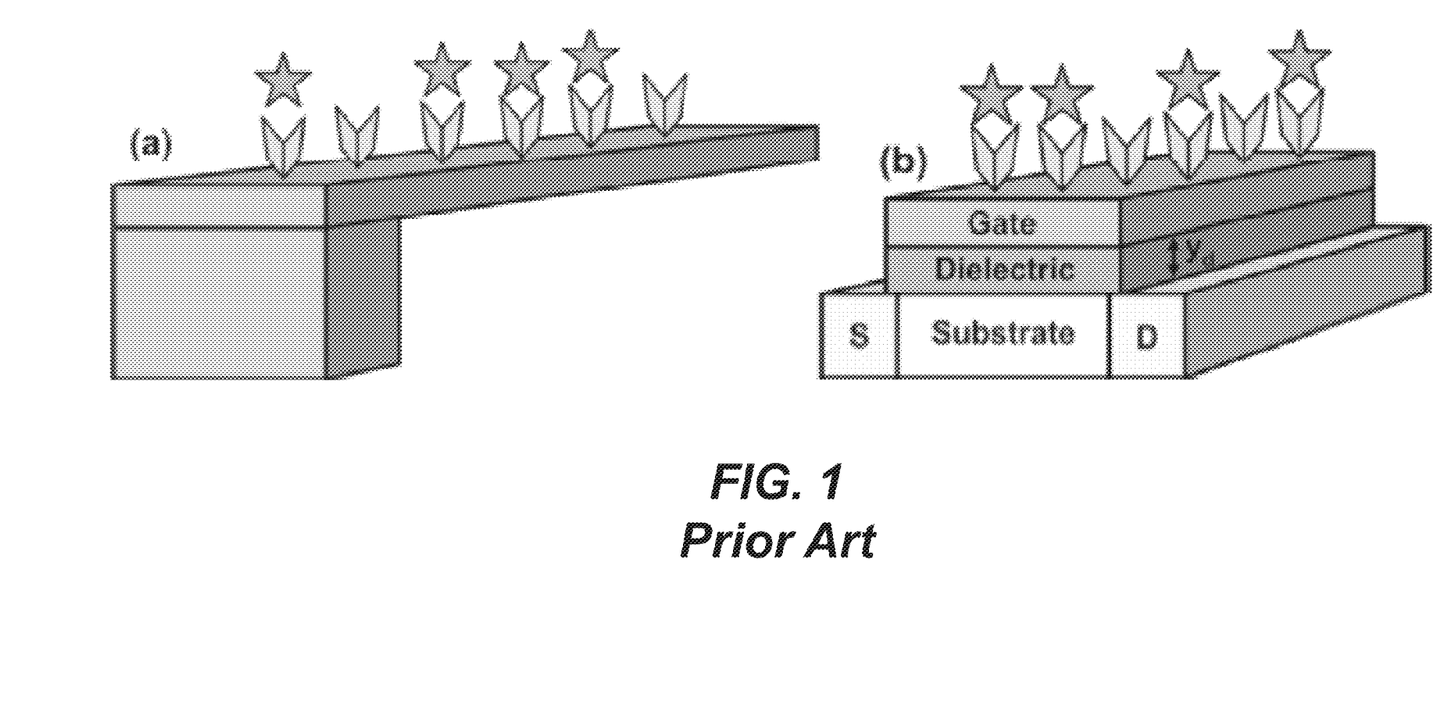
FIG. 1 illustrates a conventional mechanical particle detection device and a conventional electrical particle detection device.

Nanoscale devices are widely regarded as potential candidates for ultra-sensitive, label-free detection of bio-chemical molecules. Among the various technologies, much recent research has been devoted to mechanical and electrical biosensors. However, these technologies are plagued by many challenges in their path to further optimization. Consider, for example, mechanical biosensors such as nanocantilevers. FIG. 1(a) illustrates a conventional nanocantilever. Here, the capture of target molecules on the cantilever surface can modulate the cantilever's mass, stiffness, or introduce an additional surface stress. This change in mechanical properties of the cantilever can then be observed as a change in its resonance frequency or beam deflection. Detection schemes (like an optical detection scheme) utilize complex instrumentation to detect these changes in mechanical properties, which precludes them from many low cost, point-of-care applications. Further, the response of mechanical biosensors varies linearly with change in mass/surface stress of cantilevers, and, therefore, may often not be sensitive enough to detect target molecules at low concentrations at the early stages of onset of a disease.

On the other hand, conventional electrical biosensors (such as the ion-sensitive field-effect transistor ("ISFET") illustrated in FIG. 1(b)) sense the modulation of gate surface potential due to the presence of charged biomolecules. These conventional electrical biosensors operate in a solution that contains, not only the charged target particles that are desired to be detected, but also other charged particles. Moreover, these conventional electrical biosensors use a reference electrode to keep the potential of the solution fixed for stable measurements. The presence of other charged particles in the solution screens the charge of the particles to be detected and is referred to as "electrostatic screening". Electrostatic screening, therefore, hinders target particle detection sensitivity. In addition, electrical biosensors face an uphill challenge of miniaturization due to the use of their reference electrodes, especially for lab-on-chip applications. Further, electrical biosensors respond to charged biomolecules and, hence, are not suitable for detecting the presence of any non-charged particles.

Accordingly, a need exists in the art for improved label-free particle detection systems.

SUMMARY

The above-described problems are addressed and technical solutions are achieved in the art by transistor-based particle detection systems and methods according to various embodiments of the present invention.

In some embodiments of the present invention, a transistor includes a gate and is configured to detect at least a non-charged particle secured to the gate. The transistor may be a nanoelectromechanical field effect transistor ("NEMFET"). The transistor may include one or more receptor particles on the gate that secure(s) the non-charged particle. The transistor may be configured to change current flow through the transistor in response to a change in stiffness of the gate caused by securing of the non-charged particle to the gate. The transistor may be configured to detect the non-charged particle at least from the change in current flow. In some embodiments, the transistor includes a dielectric and a supporting structure contacting the gate and separating the gate from the dielectric. In some embodiments, the transistor is configured to cause the gate to bend away from the dielectric in response to the change in stiffness of the gate caused by the securing of the non-charged particle to the gate. The change in stiffness may be an increase in stiffness. In some embodiments, the supporting structure contacts the gate in a configuration configured to allow the gate to flex towards the dielectric at a location on a surface of the gate, the location not contacted by the supporting structure, and the surface facing the dielectric. The location on the surface of the gate may be exposed to air or another gas. In some embodiments, the supporting structure contacts the gate at least at two separated locations, but does not contact the gate at a location between at least two of the at least two separated locations.

In some embodiments, a transistor-based particle detection device includes a gate, a dielectric, and a supporting structure contacting the gate and separating the gate from the dielectric. The transistor-based particle detection device may be configured to have a near pull-in bias and a sub-threshold region bias. The near pull-in bias may be a bias where an effective stiffness of the gate is zero or substantially zero, and a relatively small change in the effective stiffness due to securing of particles by receptor particles on the gate results in a relatively large change in separation distance between the gate and the dielectric. The sub-threshold region bias may be a bias where current through the transistor-based particle detection device changes or is predisposed to change by a relatively large amount in response to a relatively small change in separation distance between the gate and the dielectric as compared to an inversion region bias, where current through the transistor-based particle detection device is relatively constant in response to changes in separation distance between the gate and the dielectric. In some embodiments, the supporting structure supports the gate in a configuration configured to allow the gate to flex towards the dielectric at a location on a surface of the gate, the location not contacted by the supporting structure, and the surface facing the dielectric. In some embodiments, the transistor-based particle detection device is a nanoelectromechanical field effect transistor ("NEMFET").

In some embodiments, the transistor-based particle detection device includes a substrate adjacent at least the dielectric and comprising a doping, a source adjacent at least the substrate, and a drain adjacent at least the substrate. The gate and the dielectric may have a separation distance between them, and the gate may have a stiffness. The gate and the source may be configured to receive a voltage, and the transistor-based particle detection device may be configured to have the near pull-in bias and the sub-threshold region bias due at least to (a) the separation distance between the gate and the dielectric, (b) the voltage, (c) the doping of the substrate, (d) the stiffness of the gate, or some or all of (a), (b), (c), and (d).

In some embodiments, a transistor-based particle detection device includes a transistor and a data processing device system. The transistor may include a gate and may be configured to change a characteristic of energy passed through the transistor in response to a change in stiffness of the gate due to a change in a number of particles secured to the gate. The processing device system may be communicatively connected to the transistor and may be configured to detect the change in the characteristic of the energy passing through the transistor as a detection of the particles secured to the gate.

In addition to the embodiments described above, further embodiments will become apparent by reference to the drawings and by study of the following detailed description.

BRIEF DESCRIPTION OF THE DRAWINGS

The present invention will be more readily understood from the detailed description of embodiments presented below considered in conjunction with the attached drawings, of which.

It is to be understood that the attached drawings are for purposes of illustrating the concepts of the invention and may not be to scale.

DETAILED DESCRIPTION

Some embodiments of the present invention pertain to a particle detection transistor, which may be a nanoelectromechanical field effect transistor (NEMFET) based biosensor, that overcomes fundamental limitations of current mechanical and electrical nanobiosensors. It should be noted, however, that the present invention is not limited to NEMFET based biosensors and includes other transistor types and includes the detection of other particle types besides biological particles, such as, but not limited to, non-biological chemical or gas sensing. In some embodiments, a gate of the particle detection transistor is fixed on two ends and is sometimes referred to herein as a "fixed-fixed beam". A change in stiffness of such a gate due to capture of target molecules causes a corresponding modulation in drain current of the particle detection transistor, in some embodiments, Such drain current modulation is detected, in some embodiments, to indicate detection of target particles. In some embodiments, such drain current modulation is maximized or at least increased when the particle detection transistor (such as a NEMFET) is biased near pull-in and in a subthreshold region, which may increase sensitivity exponentially. A particle detection transistor, according to some embodiments of the present invention, is well suited to detect the presence of not only charged particles, but also non-charged particles, and offers orders of magnitude change in sensor characteristics for small changes in beam stiffness.

It is noted that, although various devices and systems are disclosed herein, the invention includes any method of using a device or system according to any embodiment of the present invention to detect one or more target particles, including, but not limited to, non-charged particles.

It also is noted that reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, the appearances of the phrases "in one embodiment" or "in an embodiment" or "in an example embodiment" or "in this illustrated embodiment" or "in this particular embodiment" and the like in various places throughout this specification are not necessarily all referring to one embodiment or a same embodiment. Furthermore, the particular features, structures, or characteristics of different embodiments may be combined in any suitable manner to form one or more other embodiments.

It additionally is noted that, unless otherwise explicitly noted or required by context, the word "or" is used in this disclosure in a non-exclusive sense. In addition, unless otherwise explicitly noted or required by context, the word "set" is intended to mean one or more, and the word "subset" is intended to mean a set having the same or fewer elements of those present in the subset's parent or superset.

Further, the phrase "at least" is used herein to emphasize the possibility that other elements can exist besides those explicitly listed. However, unless otherwise explicitly noted (such as by the use of the term "only") or required by context, non-usage herein of the phrase "at least" includes the possibility that other elements exist besides those explicitly listed. For example, the phrase, 'based at least upon A' includes A, as well as one or more other additional elements besides A. In the same manner, the phrase, "based upon A" includes A, as well as one or more other additional elements besides A. However, the phrase, 'based only upon A' includes only A.

The term "program" in this disclosure should be interpreted as a set of instructions or modules that can be executed by one or more components in a system, such as a controller system or data processing device system, in order to cause the system to perform one or more operations. The set of instructions or modules can be stored by any kind of memory device, such as those described subsequently with respect to the memory device system 230 shown in FIG. 2. In addition, this disclosure may describe that the instructions or modules of a program are configured to cause the performance of an action. The phrase "configured to" in this context is intended to include at least (a) instructions or modules that are presently in a form executable by one or more data processing devices to cause performance of the action (e.g., in the case where the instructions or modules are in a compiled and unencrypted form ready for execution), and (b) instructions or modules that are presently in a form not executable by the one or more data processing devices, but could be translated into the form executable by the one or more data processing devices to cause performance of the action (e.g., in the case where the instructions or modules are encrypted in a non-executable manner, but through performance of a decryption process, would be translated into a form ready for execution). The word "module" can be defined as a set of instructions.

The word "device" and the phrase "device system" both are intended to include one or more physical devices or sub-devices (e.g., pieces of equipment) that interact to perform one or more functions, regardless of whether such devices or sub-devices are located within a same housing or different housings. In this regard, the word "device", may equivalently be referred to as a "device system".

Further, the phrase "in response to" may be used in this disclosure. For example, this phrase might be used in the following context, where an event A occurs in response to the occurrence of an event B. In this regard, such phrase includes, for example, that at least the occurrence of the event B causes or triggers the event A.

Figure 2:
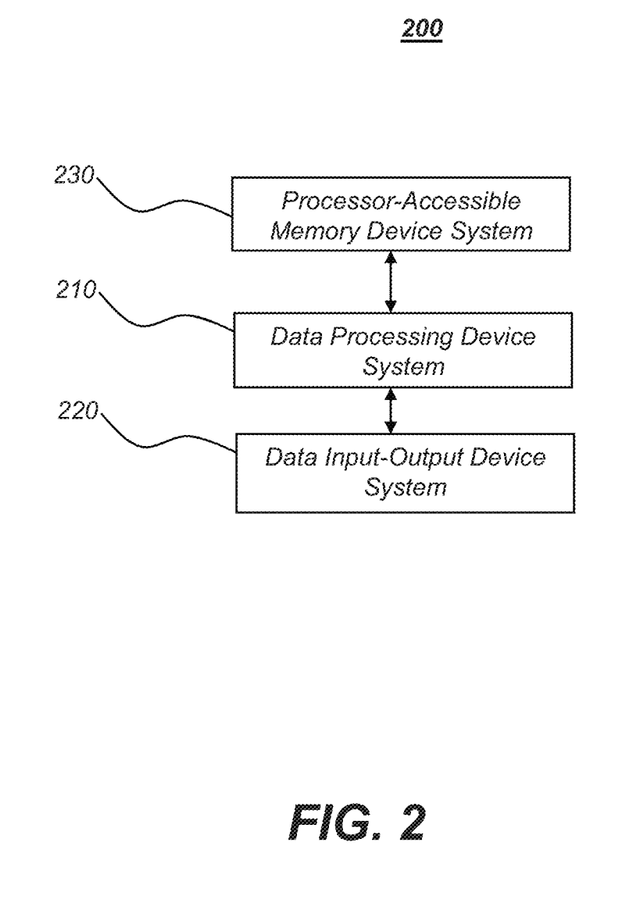
FIG. 2 illustrates a transistor-based particle detection device system, according to some embodiments of the present invention.

FIG. 2 illustrates a transistor-based particle detection system 200, according to some embodiments of the present invention. The system 200 may include a data processing device system 210, an input-output device system 220, and a processor-accessible memory device system 230. The processor-accessible memory device system 230 and the input-output device system 220 are communicatively connected to the data processing device system 210.

The data processing device system 210 includes one or more data processing devices that implement or execute, in conjunction with other devices, such as those in the system 200, methods of various embodiments of the present invention. Each of the phrases "data processing device", "data processor", "processor", and "computer" is intended to include any data processing device, such as a central processing unit ("CPU"), a desktop computer, a laptop computer, a mainframe computer, tablet computer, a personal digital assistant, a cellular phone, and any other device for processing data, managing data, or handling data, whether implemented with electrical, magnetic, optical, biological components, or otherwise.

The memory device system 230 includes one or more processor-accessible memory devices configured to store information, including the information needed to execute the methods of various embodiments. The memory device system 230 may be a distributed processor-accessible memory device system including multiple processor-accessible memory devices communicatively connected to the data processing device system 210 via a plurality of computers and/or devices. On the other hand, the memory device system 230 need not be a distributed processor-accessible memory system and, consequently, may include one or more processor-accessible memory devices located within a single data processing device.

Each of the phrases "processor-accessible memory" and "processor-accessible memory device" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs. In some embodiments, each of the phrases "processor-accessible memory" and "processor-accessible memory device" is intended to include a non-transitory computer-readable storage medium. And in some embodiments, the memory device system 230 can be considered a non-transitory computer-readable storage medium system.

The phrase "communicatively connected" is intended to include any type of connection, whether wired or wireless, between devices, data processors, or programs in which data may be communicated. Further, the phrase "communicatively connected" is intended to include a connection between devices or programs within a single data processor, a connection between devices or programs located in different data processors, and a connection between devices not located in data processors at all. In this regard, although the memory device system 230 is shown separately from the data processing device system 210 and the input-output device system 220, one skilled in the art will appreciate that the memory device system 230 may be located completely or partially within the data processing device system 210 or the input-output device system 220. Further in this regard, although the input-output device system 220 is shown separately from the data processing device system 210 and the memory device system 230, one skilled in the art will appreciate that such system may be located completely or partially within the data processing system 210 or the memory device system 230, depending upon the contents of the input-output device system 220. Further still, the data processing device system 210, the input-output device system 220, and the memory device system 230 may be located entirely within the same device or housing or may be separately located, but communicatively connected, among different devices or housings. In the case where the data processing device system 210, the input-output device system 220, and the memory device system 230 are located within the same device, the system 200 of FIG. 2 can be implemented by a single application-specific integrated circuit (ASIC) in some embodiments.

The input-output device system 220 may include a mouse, a keyboard, a touch screen, another computer, a processor-accessible memory device, or any device or combination of devices from which a desired selection, desired information, instructions, or any other data is input to the data processing device system 210. The input-output device system may include a user-activatable control system that is responsive to a user action. The input-output device system 220 may include any suitable interface for receiving information, instructions or any data from other devices and systems described in various ones of the embodiments.

The input-output device system 220 also may include an image generating device system, a display device system, a processor-accessible memory device, or any device or combination of devices to which information, instructions, or any other data is output by the data processing device system 210. The input-output device system 220 may include any suitable interface for outputting information, instructions or data to other devices and systems described in various ones of the embodiments.

If the input-output device system 220 includes a processor-accessible memory device, such memory device may or may not form part or all of the memory device system 230.

In some embodiments, the input-output device system 220 includes one or more, and in some embodiments, many of the particle detection transistors of at least one embodiment of the present invention, as each particle detection transistor may provide information to the data processing device system 210 (e.g., changes in one or more electrical characteristics of the particle detection transistor, such as change in current, to facilitate detection of target particles) and may receive information from the data processing device system 210 (e.g., one or more voltages for controlling operation of the particle detection transistor). For example, the input-output device system 220 may include a plurality of particle detection transistors according to that shown in FIG. 3, FIG. 11, or both, discussed below. When multiple particle detection transistors are utilized, they may be formed on a single integrated circuit chip, or on a plurality of integrated circuit chips, each with a plurality of particle detection transistors.

Figure 3:
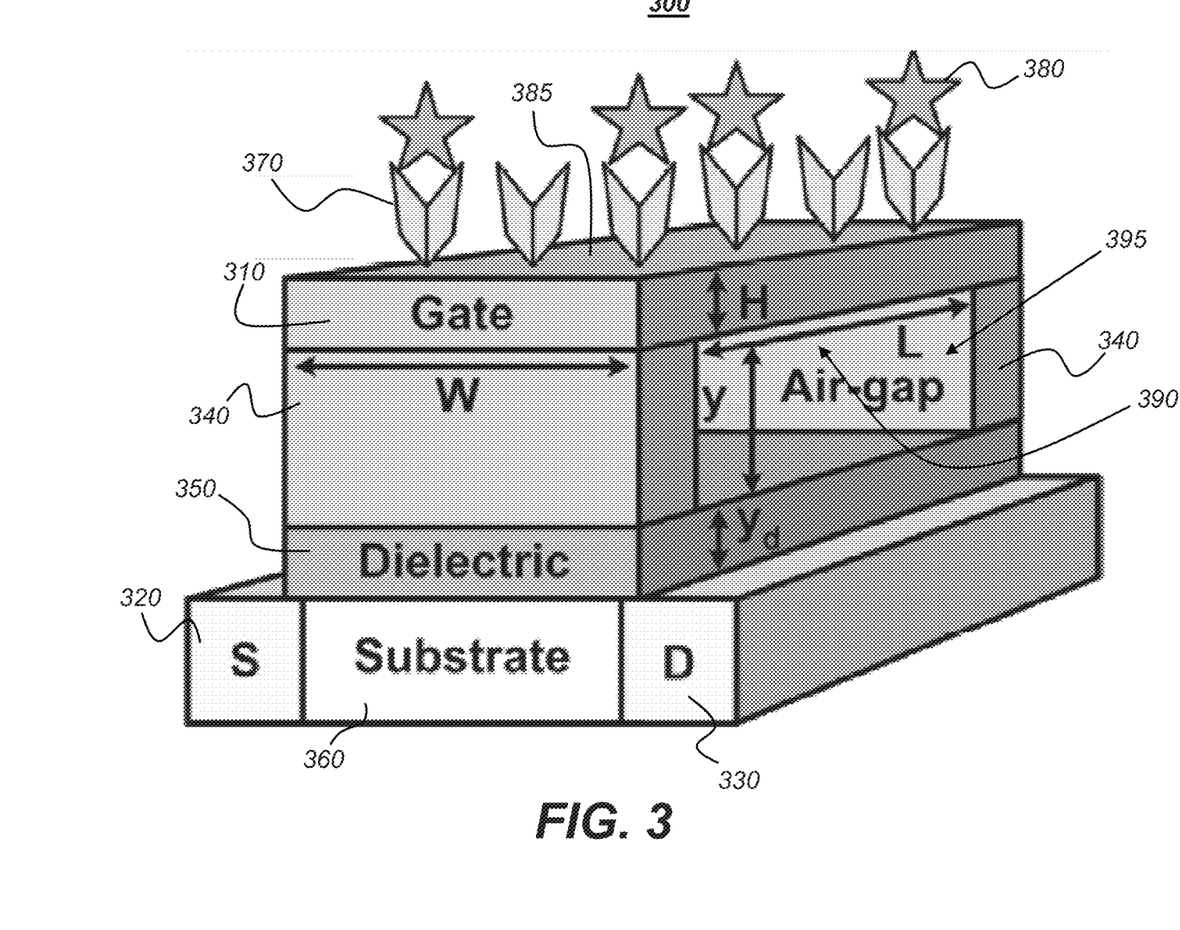
FIG. 3 illustrates a particle detection transistor, which may be part of the transistor-based particle detection device system of FIG. 1, according to some embodiments of the present invention.
Figure 4:
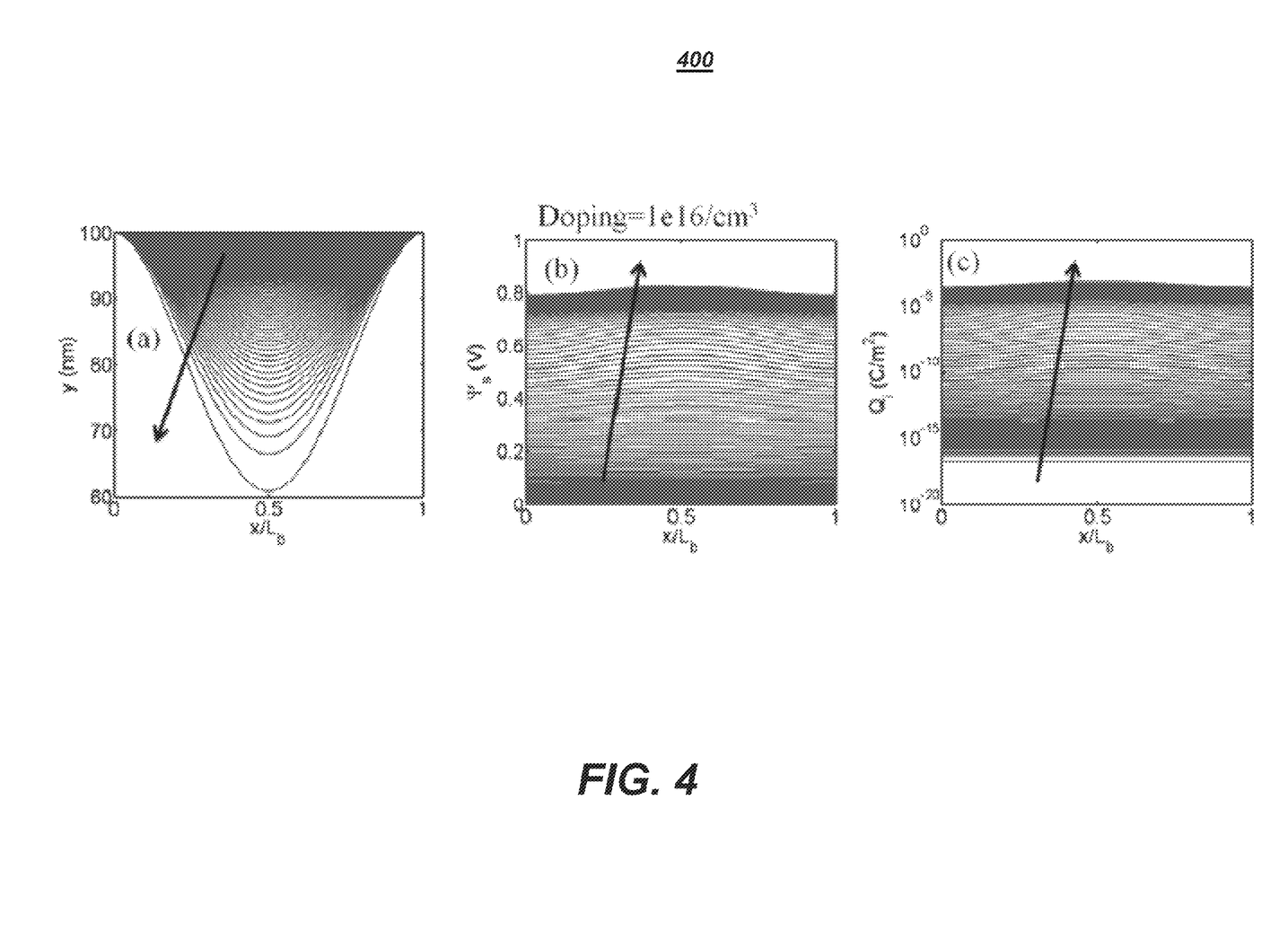
FIG. 4 illustrates gate shape, surface potential, and inversion charge characteristics of a particle detection transistor, according to some embodiments of the present invention.

In this regard, FIG. 3 illustrates a particle detection transistor 300, which may be part of the transistor-based particle detection device system of FIG. 2, according to some embodiments of the present invention. It should be noted that the transistor 300 may be manufactured using any technique known in the art, and that the invention is not limited to any particular method of manufacturing the transistor 300.

To overcome disadvantages of both conventional mechanical biosensors (e.g., FIG. 1(*a*), poor sensitivity and difficult instrumentation) and conventional electrical biosensors (e.g., FIG. 1(*b*), screening due to presence of other ions/molecules, miniaturization of reference electrode, and insensitivity to non-charged molecules), the particle detection transistor of FIG. 3 and detection device system of FIG. 2 are configured to detect particles both mechanically and electrically, according to some embodiments of the present invention, as elaborated upon below.

In the example of FIG. 3, the transistor 300, which may be a NEMFET, includes a gate 310 (which may be made of polysilicon, but is not limited thereto), a source 320 (which may be made of n-type silicon, but is not limited thereto), and a drain 330 (which may be made of n-type silicon, but is not limited thereto). A supporting structure 340, which is illustrated by two walls in FIG. 3, for example, may be made of polysilicon, but is not limited thereto. The supporting structure 340 may contact the gate 310 and separate the gate 310 from a dielectric 350, which may be made of silicon dioxide, but is not limited thereto. The dielectric 350 may be located on or adjacent a substrate 360, which may be made of p-type silicon, but is not limited thereto. The substrate may be located between or adjacent the source 320 and the drain 330. Because the supporting structure 340 in the example of FIG. 3 includes two walls fixedly supporting the gate 310, the gate 310 may be referred to as a "fixed-fixed beam" in some embodiments. In this regard, the supporting structure 340, according to some embodiments, supports the gate 310 in a configuration configured to allow the gate to flex towards, away from, or both towards and away from (i.e., at different times) the dielectric 350 at a location on a surface of the gate that is not directly supported by the supporting structure 340. For example, such a location in FIG. 3 may be defined to reside within a flex region of the gate 310, and, in some embodiments, this flex region may be defined to be a region of the gate 310 that is at least not directly above a contact point between a wall of the supporting structure 340 and the gate 310. In some embodiments, this flex region of the gate 310 is on an underneath surface 390 of the gate 310 that is not contacted by the supporting structure 340 and that faces the dielectric 350. In other words, it can be stated that in some embodiments, the supporting structure 340 contacts the gate 310 in a configuration configured to allow the gate 310 to flex or bend towards the dielectric 350 at a location on a surface (e.g., underneath surface 390) of the gate 310, the location not contacted by the supporting structure 340, and the surface (e.g., underneath surface 390) facing the dielectric 350.

In some embodiments, as shown in the example of FIG. 3, the flexing of the gate 310 is facilitated by the underneath surface 390 being exposed to a separation region 395 between the gate 310 and the dielectric 350, the separation region 395 being caused, at least in part, by the supporting structure 340. In some embodiments, the separation region 395 is filled with air or another gas, which causes the underneath surface 390 of the gate 310 to be exposed to the air or other gas. However, the invention is not limited to the separation region 395 being filled with air or another gas, and any material that allows flexing of the gate 310 toward, away from, or both toward and away from the dielectric 350 may be used.

With the transistor configuration shown, for example, in FIG. 3, the gate 310 is able to flex in response to a change in stiffness of the gate 310 due to the securing of target particles 380 (which are to be detected; only one called-out by reference numeral in FIG. 3 for purposes of clarity) to the gate 310 via receptor particles 370 (only one called-out by reference numeral in FIG. 3 for purposes of clarity) known in the art and which are attached to the gate 310, according to some embodiments. To elaborate, in some embodiments, receptor particles 370 are located on and may be attached to a detection surface 385 of the gate 310 using techniques known in the art. In some embodiments, the detection surface 385 is on an opposite side of the gate 310 as compared to the underneath surface 390 of the gate 310 and faces away from the dielectric 350.

As target particles 380 are captured or secured by the receptor particles 370, the stiffness of the gate 310 increases, because the secured target particles 380 cause an effect akin to increasing a thickness of the gate 310, much like the stiffness of a thin object increases as the thickness of the object increases. If the gate 310, along with its receptor particles 370, is predisposed to bend towards the dielectric 350 in a default non-detection state, the increase in stiffness of the gate 310 due to the capturing or securing of target particles 380 causes the gate 310, or at least a region or location (such as a central or other region/location not directly supported by the supporting structure 340) of the gate 310, to move or bend away from the dielectric 350. This movement of the gate 310 away from the dielectric 350 changes the characteristics of the transistor 300 (e.g., turn-on voltage, capacitance, current flow through the transistor at a fixed gate-source voltage, transconductance etc.) which can be used by the system (e.g., FIG. 2) to detect the capturing of the target particles 380.

In this regard, the movement of the gate 310 is a mechanical action of the transistor 300 that causes changes in the electrical characteristics of the transistor 300 to facilitate detection of the target particles 380. At least because this mechanical action of the transistor 300 is caused by the securing of the target particles 380 to the gate 310, and at least because the target particles 380 can be secured to the gate 310 (e.g., by receptor particles 370) regardless of the charge of the target particles 380, the transistor 300 is configured to detect non-charged target particles. For example, the transistor 300 is configured, in some embodiments, to change its current flow through the transistor 300 in response to the change in stiffness of the gate 310 caused by securing of non-charged particles to the gate 310, and at least this change in current flow can be sensed (e.g., by the system 200 in FIG. 2) to detect the non-charged particles. For another example, the transistor 300, in some embodiments, is configured to change a characteristic of energy passed through the transistor 300 in response to a change in stiffness of the gate 310 due to a change in a number of particles 380 secured to the gate 310. In some of embodiments, a processing device system (e.g., the data processing device system 210) is communicatively connected to the transistor 300 and is configured to detect the change in the characteristic of the energy passing through the transistor 300 (or some other detectable change in characteristic of the transistor 300) as a detection of the particles 380 secured to the gate.

However, the invention is not limited to the detection of non-charged particles and applies to the detection of any target particle (charged or non-charged) that can cause a change in detectable characteristics of the transistor 300 due to flexing or bending of the gate 310.

At least because the transistor 300 changes at least its detectable electrical characteristics due to the securing of target particles 380 to the gate 310, easier detection-information read-out as compared to conventional mechanical biosensors (e.g., FIG. 1(a)) is achieved. Further, detection of the target particles 380 may be performed by a data processing device system (e.g., FIG. 2) that senses these changes in electrical characteristics of the transistor 300, and complex optical detection schemes like those used for conventional mechanical biosensors are not necessary. Further still, because the detection mechanism does not depend on the charge of the target particles, use of a reference electrode, like those used by conventional electrical biosensors, is not required, and, consequently, improved detection device size reduction can be achieved as compared to conventional electrical biosensors. In addition, because the detection mechanism need not be charged based, problems associated with hindrance of sensitivity by electrostatic screening due to the presence of other charged ions/molecules in a solution in which the sensor is operating can be avoided.

Although the transistor 300 in FIG. 3 illustrates the supporting structure 340 contacting the gate at two separated locations (e.g., at the respective ends of the gate 310), but not contacting the gate 310 at a location (e.g., residing in a flex region of the gate 310 on the underneath surface 390 of the gate 310 not contacting the respective ends of the gate 310) between the two separated locations, it should be noted that the invention is not limited to such a configuration. In this regard, the invention includes any configuration that allows a change in detectible characteristics of the transistor 300 due to flexing or bending of the gate 310 due to detection of target particles 380.

Figure 11:
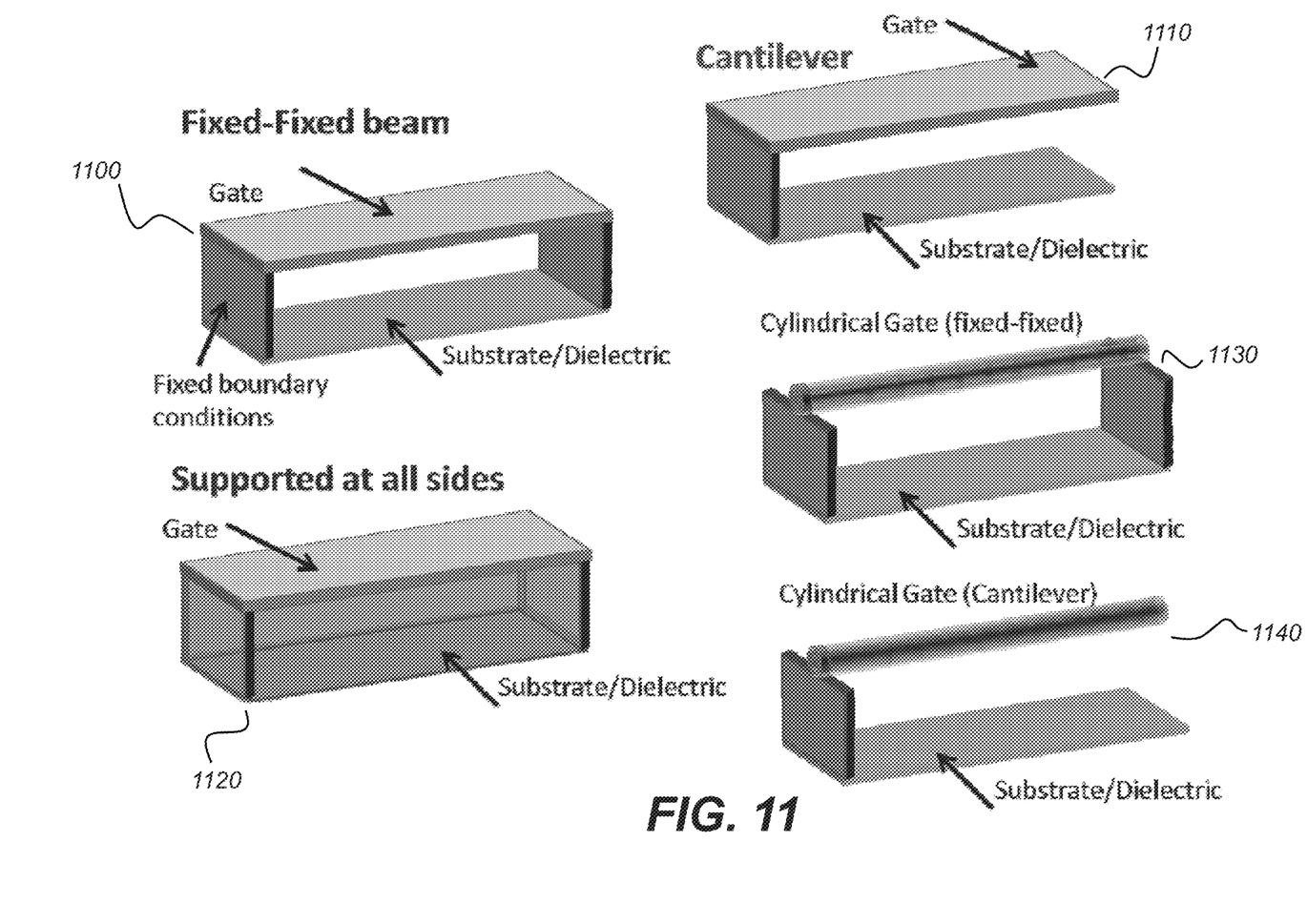
FIG. 11 illustrates alternate particle detection transistor, according to various embodiments of the present invention.

For example, in some embodiments, the supporting structure 340 contacts or otherwise supports the gate 310 at only a single contiguous region (e.g., omit one of the walls of the supporting structure 340 in FIG. 3; see also FIG. 11, cantilever configuration 1110). On the other hand, in some embodiments, the supporting structure 340 contacts or otherwise supports the gate 310 at more than two contiguous regions. For example, the gate 310 in FIG. 3 may be supported by four 'pillars', one at each corner of the gate 310, instead of being supported by two walls like the supporting structure 340 of FIG. 3.

Further, the gate 310 need not be of rectangular shape, as shown in FIG. 3. In this regard, it is noted that the invention is not limited to the particular transistor configuration shown in FIG. 3, and the invention includes any shape of the gate 310, the supporting structure 340, or any other element of the transistor 300 in FIG. 3, as well as any arrangement of the elements of the transistor 300 in FIG. 3 that allows a change in detectible characteristics of the transistor 300 due to flexing or bending of the gate 310 due to detection of target particles 380.

In this regard, FIG. 11 illustrates some other configurations of the transistor 300, according to various embodiments of the present invention. Fixed-fixed beam configuration 1100 represents a gate, supporting structure, and substrate/dielectric according to the configuration of FIG. 3. Cantilever configuration 1110 is similar to the structure of fixed-fixed beam configuration 1100, but includes a supporting structure of only a single support wall. FIG. 11 also illustrates a configuration 1120 in which the gate is supported at all sides. In addition, FIG. 11, illustrates that the gate need not be flat and, may, for example, have a cylindrical shape, as shown by fixed-fixed beam configuration 1130 and cantilever configuration 1140. A cylindrical gate shape, for example, may be implemented using a carbon nanotube or silicon nanowire.

In some embodiments, to enhance the sensitivity of particle detection of the transistor 300, the transistor 300 is configured to have a near pull-in bias and a sub-threshold region bias. The near pull-in bias may be described as a bias where an effective stiffness of the gate 310 is zero or substantially zero, and a relatively small change in the stiffness due to securing of particles 380 by the receptor particles 370 on the gate 310 results in a relatively large change in separation distance y (e.g., FIG. 3) between the gate 310 and the dielectric 350. Effective stiffness is the sum of the mechanical stiffness (a positive quantity) of the gate and electrostatic stiffness (a negative quantity) due to the electrostatic force acting on the gate when a bias is applied. At a zero-bias condition, effective stiffness is the same as the mechanical stiffness of the gate and at pull-in bias effective stiffness is zero.

The sub-threshold region bias may be described as a bias where current through the transistor-based particle detection device (e.g., transistor 300) changes or is predisposed to change by a relatively large amount in response to a relatively small change in separation distance y between the gate 310 and the dielectric 350 as compared to an inversion region bias, where current through the transistor-based particle detection device (e.g., transistor 300) is relatively constant in response to changes in separation distance y between the gate 310 and the dielectric 350.

In other words, the near pull-in bias of the transistor 300 allows the gate 310 to be predisposed to move by a relatively large amount in response to the securing of a relatively small number of target particles 380 to the gate 310. The sub-threshold region bias allows electrical characteristics of the transistor 300 to change by a relatively large amount in response to a relatively small change in separation distance y between the gate 310 and the dielectric 350. Each of these biases enhances a change in characteristics of the transistor 300 due to the securing of target particles 380 to the gate 310, which enhances detectability of the target particles 380. Collectively, these biases allow a relatively small number of target particles 380 secured to the gate 310 to result in a relatively large detection signal to be provided by the transistor 300 to, for example, a detection system such as system 200 in FIG. 2.

In some embodiments, the transistor 300 is configured to have the near pull-in bias and the sub-threshold bias by having a default non-detection or pre-detection-but-detection-ready state: (a) separation distance y between the gate 310 and the dielectric 350, (b) gate-source voltage, (c) substrate doping, (d) gate stiffness, or some or all of (a), (b), (c), and (d).

In this regard, the transistor 300 in FIG. 3 is modeled by coupling the Euler-Bernoulli equation with the Poisson's equation, both of which are known in the art. Equations (1)-(4), below, are used to solve the shape of the fixed-fixed beam (i.e., the gate 310) as a function of gate bias, where y(x) is the displacement of a point on the beam located at distance x away from one end of the beam, $D = EW_b H_b^3/12$ is the flexural rigidity of the fixed-fixed beam which can change when particles are captured on the beam, $E_{air}$ is the electrical field in air, $W_b$ is the width of the beam, $H_b$ is the thickness of the beam, E is the Young's modulus of the beam, $\epsilon_0$ is the permittivity of free space, $E_d$ is the electrical field in the dielectric, $E_s$ is the electric field at the dielectric-semiconductor interface, $E_d$ is the dielectric constant of the dielectric, $e_s$ is the dielectric constant of semiconductor, $V_{GB}$ is the applied gate bias, $V_{air} = y(x)E_{air}$ is the voltage drop in air, $V_d = y_d E_d$ is the voltage drop in the dielectric, $\psi_s$ is the surface potential (or voltage drop) in semiconductor, q is the charge on electron, $N_A$ is substrate doping, $k_B$ is the Boltzmann constant, T is absolute temperature and $n_i$ is the intrinsic carrier concentration in substrate. Equation (5), below, calculates the total inversion charge in the transistor, where $V_t = k_B T/q$ is the thermal voltage. Equation (6), below, calculates the total drain current in the linear region, where, $\mu_n$ is the electron mobility, $L_b$ is the length of the beam, $V_{DS}$ is the applied source-drain bias. There is no known analytical solutions of Equations (1)-(6), therefore, Equations (1)-(6) are solved numerically.

Euler-Bernoulli Equation: $\frac{\partial^2}{\partial x^2}\left(D(x)\frac{\partial^2 y}{\partial x^2}\right) = -\frac{1}{2}\varepsilon_0 E_{air}^2 W_b$  (1)

Displacement field continuity: $E_{air} = \varepsilon_d E_d = \varepsilon_s E_s$  (2)

Kirchhoff's voltage law: $V_{GB} = V_{air} + V_d + \psi_s$  (3)

$$V_{GB} = \left(y(x) + \frac{y_d}{\varepsilon_d}\right)\varepsilon_s E_s + \psi_s$$

Electric field at semiconductor surface  (4)

$$E_s = \frac{\sqrt{2q\varepsilon_s N_A}}{\varepsilon_s \varepsilon_0}$$

$$\left[\psi_s + \left(\exp\left(-\frac{q\psi_s}{k_B T}\right) - 1\right)\frac{k_B T}{q} - \frac{n_i^2}{N_A^2}\left(\psi_s - \left(\exp\left(-\frac{q\psi_s}{k_B T}\right) - 1\right)\frac{k_B T}{q}\right)\right]^{\frac{1}{2}}$$

Inversion charge in semiconductor  (5)

$$Q_i = \frac{qn_i^2}{N_A}\int_0^{\psi_i}\left(\frac{\exp\left(\frac{\psi}{V_t}\right) - 1}{E_s}\right)d\psi$$

Total drain current of NEMFET  $I_{DS} = \mu_n\left(\int_0^{L_b} Q_i dx\right)\frac{V_{DS}}{W_b}$  (6)

Figure 5:
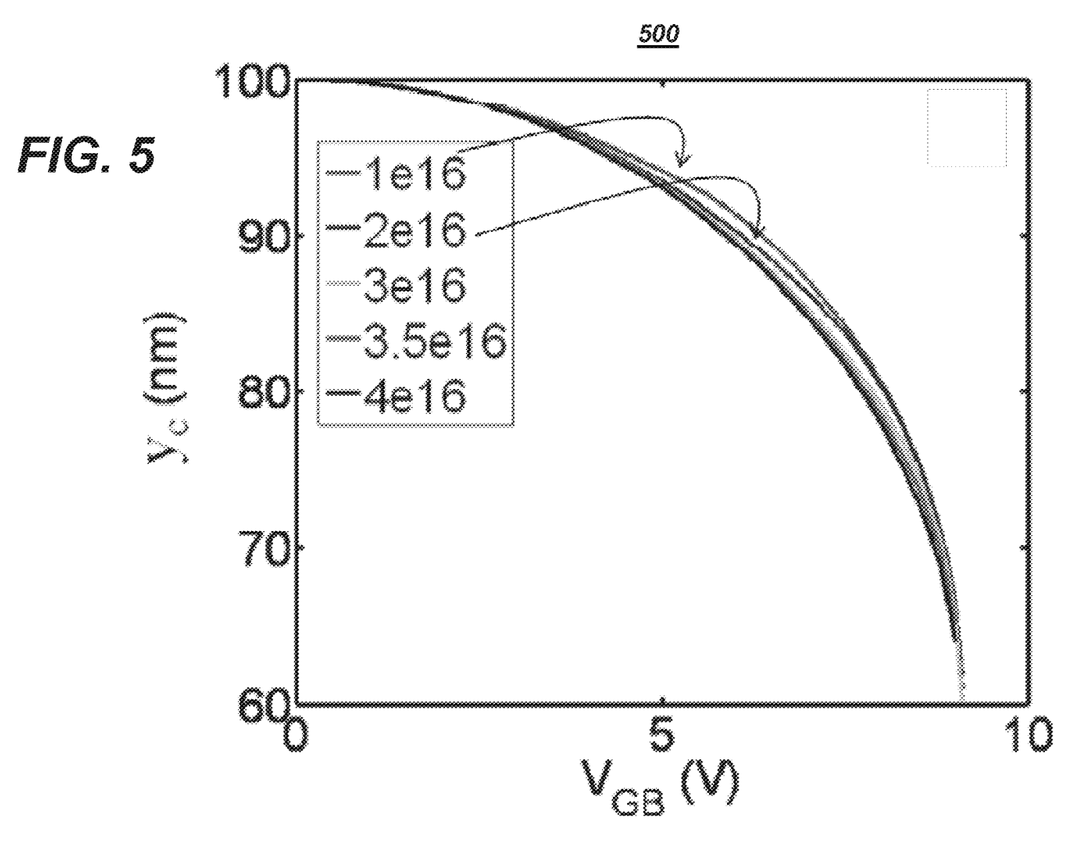
FIG. 5 illustrates displacement of the center of a gate of a particle detection transistor as a function of gate voltage for different substrate doping, according to some embodiments of the present invention.
Figure 6:
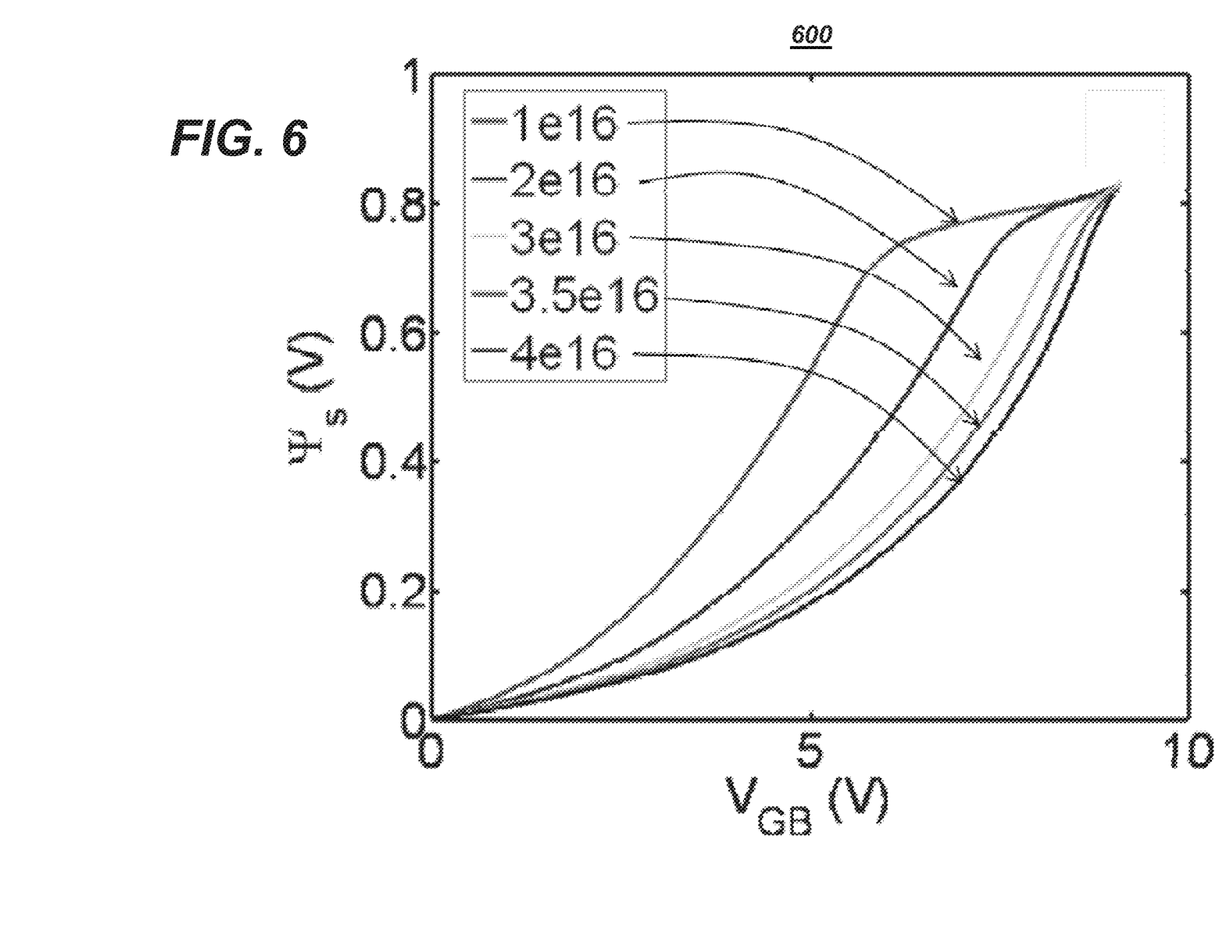
FIG. 6 illustrates surface potential at the center of a gate of a particle detection transistor as a function of gate voltage for different substrate doping, according to some embodiments of the present invention.
Figure 7:
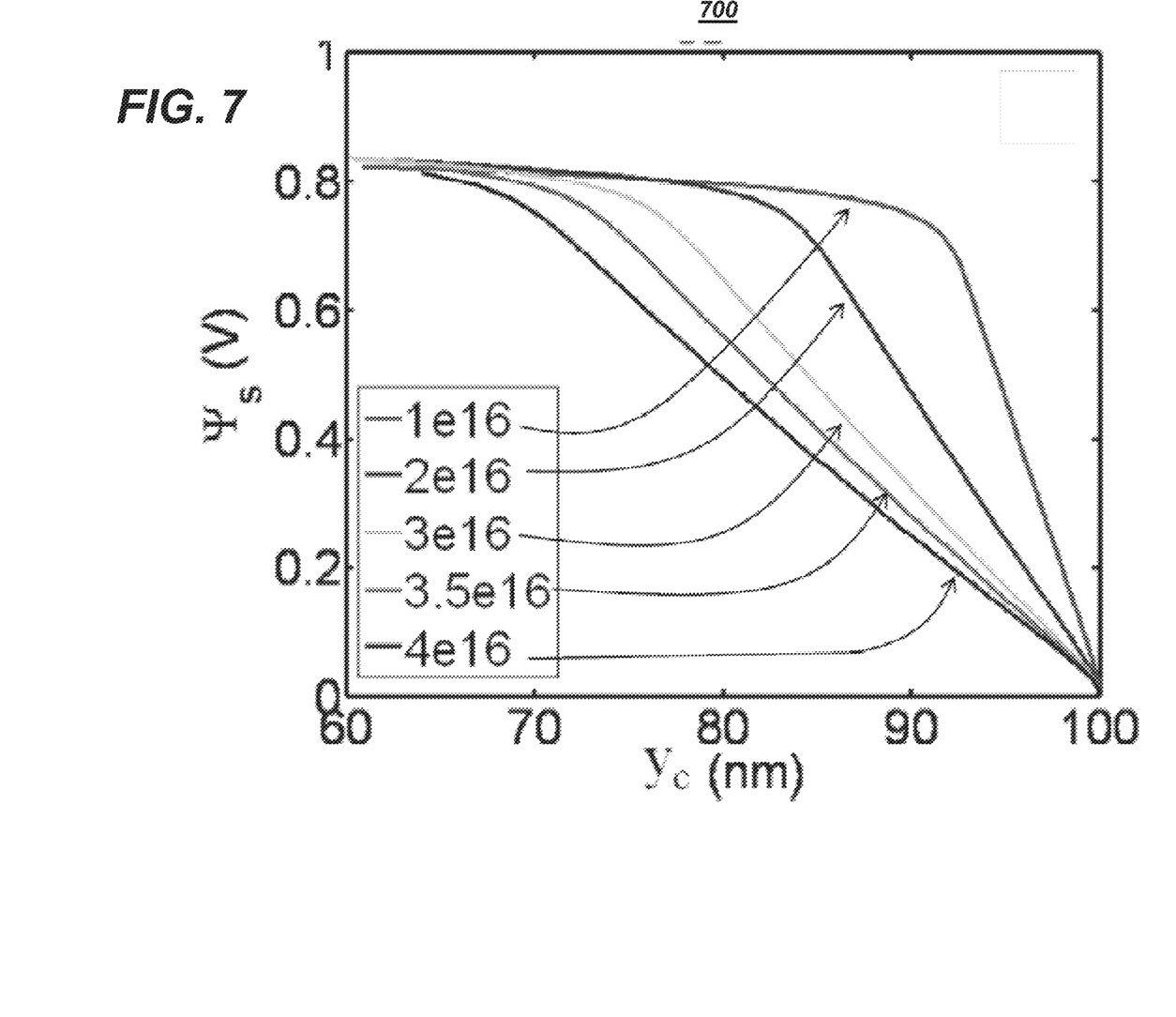
FIG. 7 illustrates surface potential just below the center of a gate of a particle detection transistor as a function of a gap between a center of a gate and a dielectric for different substrate doping, according to some embodiments of the present invention.
Figure 8:
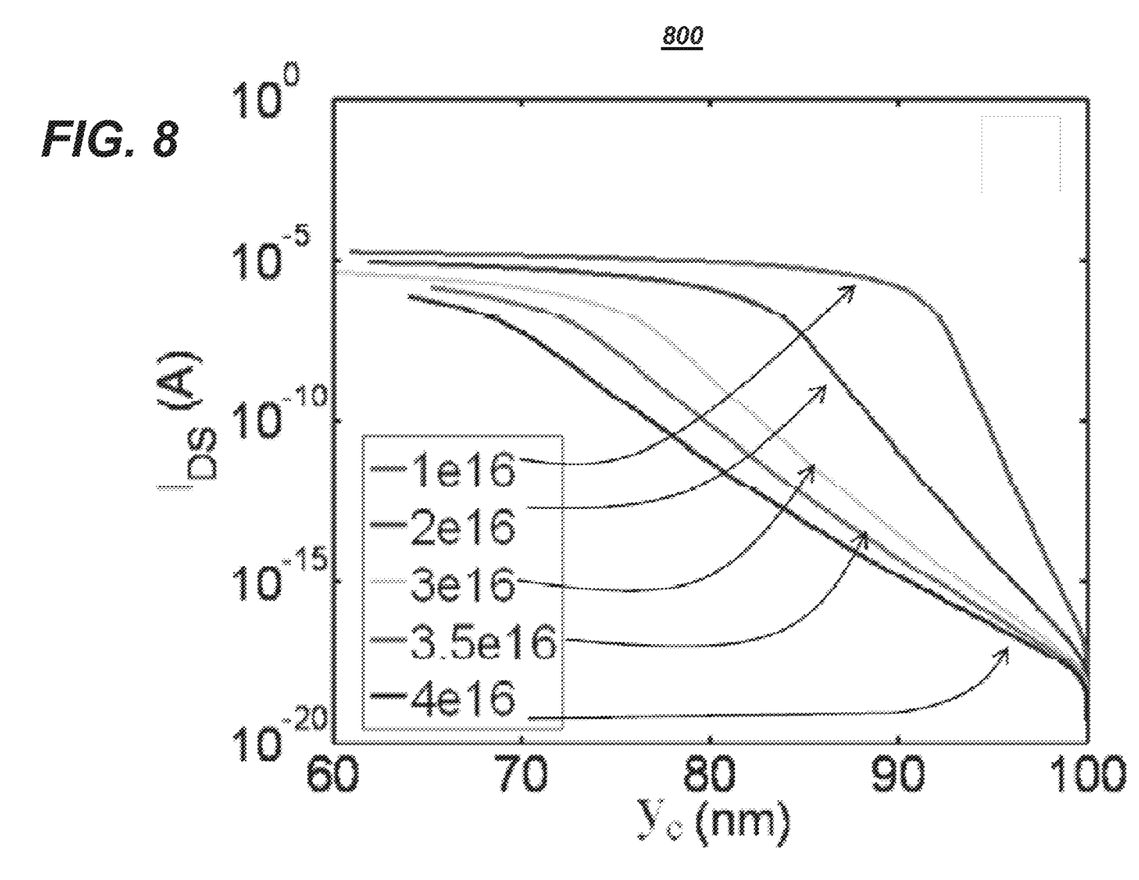
FIG. 8 illustrates drain current of a particle detection transistor as a function of a gap between a center of a gate and a dielectric for different substrate doping, according to some embodiments of the present invention.

FIGS. 2-8 depict behavior of a particle detection NEMFET (e.g., some embodiments of FIG. 3) and the effect of substrate doping on the NEMFET, according to some embodiments of the present invention. In this regard, FIG. 4(a) depicts the shape of the fixed-fixed beam for different gate voltages before pull-in (e.g., before stiffening of the gate 310 due to detection of target particles 380). FIG. 4(b) and FIG. 4(c) respectively depict surface potential and inversion charge in the length direction of the fixed-fixed beam. Gate bias $V_{GB}$ increases in the direction of the arrow in FIGS. 4(a)-4(c). Surface potential and inversion charge increases as $V_{GB}$ increases. As the voltage $V_{GB}$ increases, the fixed-fixed beam bends down towards the dielectric. FIG. 5 depicts the displacement of the center of the beam (e.g., gate 310) $y_c = y(L_b/2)$ as a function of gate bias $V_{GB}$ for different substrate doping concentrations $N_A$ (units $cm^{-3}$). It is interesting to note that $y_c$ is very sensitive to any small change in mechanical property of beam near pull-in. Any small change will result in a large change in $y_c$. Surface potential just below the center of the beam is plotted against $V_{GB}$ in FIG. 6 for different substrate doping concentrations. The plot of surface potential just below the center of the beam and drain current $I_{DS}$, as a function of $y_c$ gives more insight about the operation of the NEMFET (see FIGS. 7 and 8). It is evident that there are two regions; an inversion region in which surface potential and current is almost constant and a subthreshold region in which surface potential and current changes rapidly with displacement. If the NEMFET is biased such that it is near pull-in and in the sub-threshold region (by choosing e.g., the doping or other factors appropriately) then a small change in beam (e.g., gate 310) stiffness will result in an exponentially large change in drain current.

Figure 9:
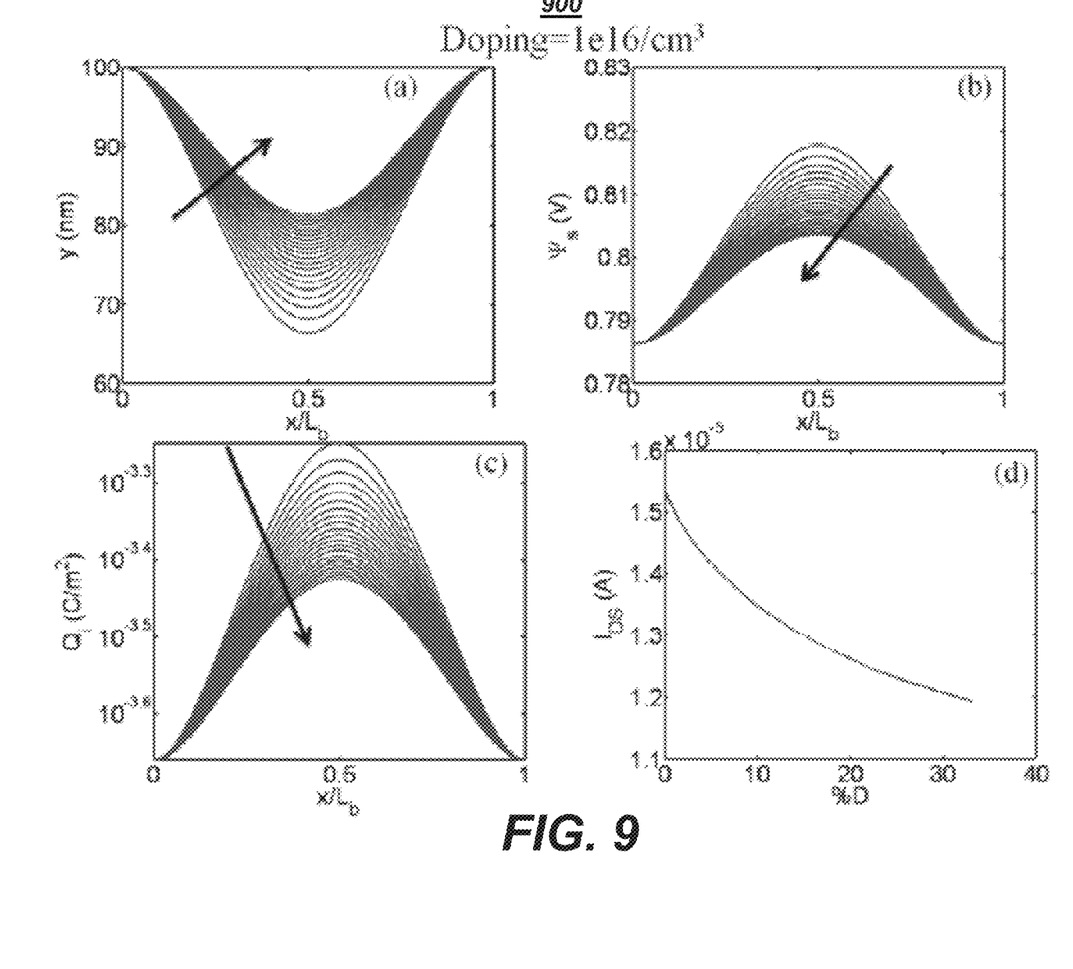
FIG. 9 illustrates sensing characteristics with respect to gate stiffness change of a particle detection transistor, according to some embodiments of the present invention.
Figure 10:
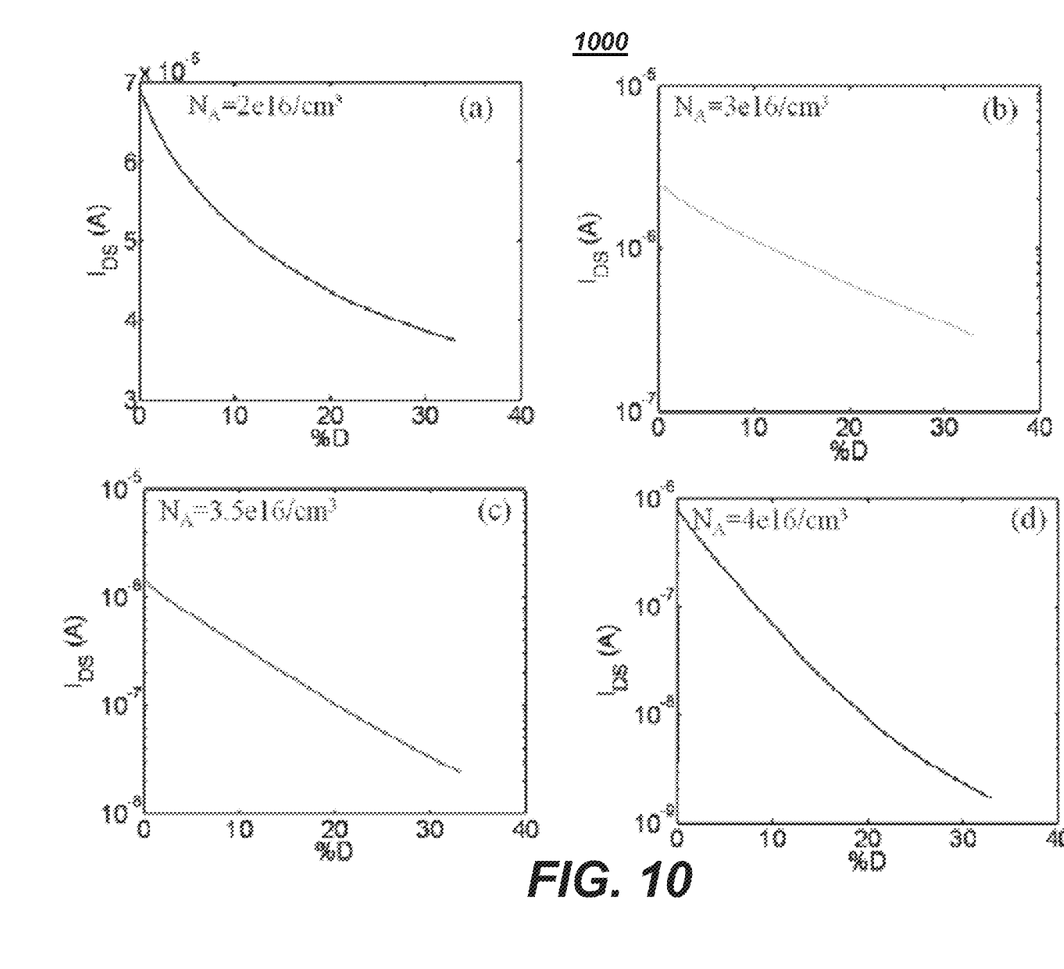
FIG. 10 illustrates the effect of substrate doping on sensitivity of a particle detection transistor, according to some embodiments of the present invention.

In some embodiments, detection of target particles 380 is achieved due to a change in the stiffness (proportional to flexural rigidity) of the beam acting as a gate of the transistor 300, with a change in drain current in the transistor 300 being observed (e.g., by the system 200 in FIG. 2) as an indication of detection of the target particles 380. In this regard, FIG. 9 depicts the effect of rigidity change on NEMFET (e.g., FIG. 3 according to some embodiments) behavior. FIG. 9(a) depicts the shape of the gate at fixed gate voltage as a function of flexural rigidity D, where stiffness is proportional to flexural rigidity. The fixed-fixed beam (e.g., the gate 310 in FIG. 3) moves upwards due to increase in D (see FIG. 9(a), where D increases in the direction of the arrow in FIGS. 9(a)-(c)). Therefore, surface potential and inversion charge are reduced as D increases (see FIGS. 9(b)-(c), respectively), with a corresponding decrease in drain current (see FIG. 9(d)). This decrease in $I_{DS}$ signals the capture of target particles 380. FIGS. 10(a)-(d) show $I_{DS}$ as a function of percentage change in D for different substrate doping concentrations. As doping increases, a decrease in $I_{DS}$, increases for a given percentage change in D. When $N_A = 4e16/cm^3$, an approximately 10% change in D results in one order of magnitude change in drain current.

It is to be understood that the above-described embodiments are merely illustrative of the present invention and that many variations of the above-described embodiments can be devised by one skilled in the art without departing from the scope of the invention. It is therefore intended that all such variations be included within the invention and the scope of the following claims and their equivalents.

What is claimed is:

1. A transistor comprising a gate and configured to detect at least a non-charged particle secured to the gate,
   wherein the transistor further comprises one or more receptor particles on the gate that secure(s) the non-charged particle, wherein the transistor is configured to change current flow through the transistor in response to a change in stiffness of the gate caused by securing of the non-charged particle to the gate, wherein the transistor is configured to detect the non-charged particle at least from the change in current flow, wherein the transistor further comprises a dielectric and a supporting structure contacting the gate and separating the gate from the dielectric, and wherein the transistor is configured to cause the gate to bend away from the dielectric in response to the change in stiffness of the gate caused by the securing of the non-charged particle to the gate.

2. The transistor of claim 1, wherein the supporting structure contacts the gate in a configuration configured to allow the gate to flex towards the dielectric at a location on a surface of the gate, the location not contacted by the supporting structure, and the surface facing the dielectric.

3. The transistor of claim 2, wherein the location on the surface of the gate is exposed to air or another gas.

4. The transistor of claim 1, wherein the supporting structure contacts the gate at least at two separated locations, but does not contact the gate at a location between at least two of the at least two separated locations.

5. The transistor of claim 4, wherein the supporting structure contacts the gate at least at four separated locations.

6. The transistor of claim 1, wherein the change in stiffness is an increase in stiffness.

7. The transistor of claim 1, wherein the supporting structure supports the gate in a cantilevered configuration.

8. The transistor of claim 1, wherein the gate is substantially flat.

9. A transistor-based particle detection device comprising:
a transistor comprising a gate, a source, a drain, a dielectric, and a substrate and configured to change a characteristic of energy passed passing through the transistor in response to a change in a stiffness in the gate due to a change in a number of particles secured to a detection surface of the gate; and a data processing device system communicatively connected to the transistor and configured to detect the change in the characteristic of the energy passing through the transistor as a detection of the particles secured to the gate, wherein the detection surface is on an opposite side of the gate as compared to an underneath surface of the gate, wherein the underneath surface of the gate faces the dielectric, wherein the dielectric is located on or adjacent the substrate, and wherein the substrate is located between or adjacent the source and the drain.

10. The device of claim 9, wherein the transistor comprises a supporting structure, the supporting structure contacting the gate and the dielectric, the supporting structure separating the gate from the dielectric.

11. The device of claim 10, wherein the supporting structure contacts the gate in a configuration configured to allow the gate to flex towards the dielectric at a location on the underneath surface of the gate, the location not contacted by the supporting structure.

12. The device of claim 11, wherein the location on the underneath surface of the gate is exposed to air or another gas.

13. The device of claim 10, wherein the supporting structure contacts the gate at least at two separated locations, but does not contact the gate at a location between at least two of the at least two separated locations.

14. The device of claim 13, wherein the supporting structure contacts the gate at least at four separated locations.

15. The device of claim 10, wherein the supporting structure contacts the gate at only a single contiguous region.

16. The device of claim 10, wherein the supporting structure supports the gate in a cantilevered configuration.

17. The device of claim 9, wherein the gate is substantially flat.

18. The device of claim 9, wherein the gate is substantially cylindrical.

19. The device of claim 9, wherein the change in stiffness is an increase in stiffness.

20. The transistor of claim 9, wherein the gate is substantially cylindrical.

* * * * *